(12) United States Patent
Bomzon et al.

(10) Patent No.: US 11,241,577 B2
(45) Date of Patent: Feb. 8, 2022

(54) GENERATING TUMOR TREATING FIELDS (TTFIELDS) WITH HIGH UNIFORMITY THROUGHOUT THE BRAIN

(71) Applicant: Novocure GmbH, Root (CH)

(72) Inventors: Zeev Bomzon, Kiryat Tivon (IL); Ariel Naveh, Haifa (IL); Ofir Yesharim, Nes Tziona (IL)

(73) Assignee: Novocure GmbH, Root (CH)

( * ) Notice: Subject to any disclaimer, the term of this patent is extended or adjusted under 35 U.S.C. 154(b) by 97 days.

(21) Appl. No.: 16/599,686

(22) Filed: Oct. 11, 2019

(65) Prior Publication Data

US 2020/0114141 A1 Apr. 16, 2020

Related U.S. Application Data

(60) Provisional application No. 62/745,689, filed on Oct. 15, 2018.

(51) Int. Cl.
| | |
|---|---|
| *A61N 1/36* | (2006.01) |
| *A61N 1/04* | (2006.01) |
| *A61N 1/40* | (2006.01) |

(52) U.S. Cl.
CPC .............. *A61N 1/36* (2013.01); *A61N 1/0408* (2013.01); *A61N 1/0492* (2013.01); *A61N 1/40* (2013.01)

(58) Field of Classification Search
CPC ...... A61N 1/0408; A61N 1/0492; A61N 1/40; A61N 1/0476; A61N 1/08; A61N 1/36;
(Continued)

(56) References Cited

U.S. PATENT DOCUMENTS 6,081,744 A * 6/2000 Loos ................. A61N 1/40
607/2
6,868,289 B2 3/2005 Palti
(Continued)

FOREIGN PATENT DOCUMENTS

WO 2018057953 A2 3/2018

OTHER PUBLICATIONS

International Search Report and Written Opinion issued for application No. PCT/IB2019/059189 dated Dec. 19, 2019.
(Continued)

*Primary Examiner* — Catherine M Voorhees
(74) *Attorney, Agent, or Firm* — Potomac Law Group, PLLC

(57) ABSTRACT

This application discloses configurations for arranging transducer arrays on a person's head to impose tumor treating fields (TTFields) in the brain at field strengths that are as uniform as possible throughout the entire brain. In some embodiments, L-shaped sets of electrodes are positioned near the right and left ears, each with a horizontal arm above the ear and a vertical arm behind the ear. Optionally, these embodiments may be combined with a second pair of electrodes positioned on top of the head and behind the neck. In other embodiments, one pair of electrodes is positioned above the right ear and on the left/rear portion of the neck; and a second pair of electrodes is positioned above the left ear and on the right/rear portion of the neck. These configurations improve the uniformity of the electric fields imposed throughout the brain, and are particularly useful for preventing and/or treating metastases.

11 Claims, 7 Drawing Sheets

(58) Field of Classification Search
CPC ............ A61N 1/36002; A61N 1/36025; A61N 1/0456; G16H 50/50; G16H 20/40; G16H 40/63
See application file for complete search history.

(56) References Cited

U.S. PATENT DOCUMENTS

| | | | |
|---|---|---|---|
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 2006/0167499 A1 | 7/2006 | Palti | |
| 2007/0239213 A1 | 10/2007 | Palti | |
| 2009/0076366 A1* | 3/2009 | Palti | A61N 1/0408 600/395 |
| 2011/0137229 A1* | 6/2011 | Palti | A61N 1/40 604/20 |
| 2012/0283726 A1 | 11/2012 | Palti | |
| 2013/0317580 A1* | 11/2013 | Simon | A61N 1/04 607/115 |
| 2015/0094557 A1* | 4/2015 | Hsu | A61B 5/282 600/391 |
| 2016/0114174 A1* | 4/2016 | Colvin | A61N 1/3787 607/46 |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1* | 1/2018 | Kirson | A61N 1/40 |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0333574 A1 | 11/2018 | Pal | |
| 2019/0117956 A1 | 4/2019 | Wenger et al. | |
| 2019/0307781 A1 | 10/2019 | Krex et al. | |
| 2019/0308016 A1 | 10/2019 | Wenger et al. | |
| 2019/0314631 A1* | 10/2019 | Wong | A61N 1/36002 |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0016399 A1 | 1/2020 | Kaynan et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2021/0077800 A1* | 3/2021 | Michalczyk | A61N 1/40 |

OTHER PUBLICATIONS

International Search Report and Written Opinion issued in application No. PCT/IB2019/058709 dated Jan. 7, 2020.

* cited by examiner

GENERATING TUMOR TREATING FIELDS (TTFIELDS) WITH HIGH UNIFORMITY THROUGHOUT THE BRAIN

CROSS REFERENCE TO RELATED APPLICATIONS

This Application claims the benefit of U.S. Provisional Application 62/745,689 filed Oct. 15, 2018, which is incorporated herein by reference in its entirety.

BACKGROUND

TTFields are low intensity (e.g., 1-4 V/cm) alternating electric fields within the intermediate frequency range (e.g., 100-300 kHz), which may be used, for example, to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed GBM patients. The alternating electric fields are induced non-invasively by transducer arrays (i.e., arrays of capacitively coupled electrodes) placed directly on the patient's head (e.g., using the Novocure Optune® system), and applying AC voltages between the transducer arrays.

For treating glioblastoma, the TTFields are delivered to patients via four transducer arrays 11-14 that are placed on the patient's skin in close proximity to a tumor (e.g., as depicted in FIGS. 1A-1D for a person with glioblastoma). The transducer arrays 11-14 are arranged in two pairs, and each transducer array is connected via a cable to an AC signal generator. The AC signal generator (a) sends an AC current through one pair of arrays 11, 12 during a first period of time, which induces an electric field with a first direction through the tumor; then (b) sends an AC current through the other pair of arrays 13, 14 during a second period of time, which induces an electric field with a second direction through the tumor; then repeats steps (a) and (b) for the duration of the treatment.

In the context of glioblastoma, conventional solutions (e.g., NovoTAL software from Novocure) are available for determining where the transducer arrays 11-14 should be placed on a subject's head in order to maximize the field strength within the tumor. But because the prior art solutions are only concerned with the field distribution within the tumor, none of the prior art solutions addressed the uniformity of the electric field in other regions of the brain.

SUMMARY OF THE INVENTION

One aspect of the invention is directed to a first method of applying an alternating electric field to a person's brain. The first method comprises affixing a first set of electrode elements to a right side of the person's head. The first set of electrode elements has an upper section positioned above the external opening of the person's tight ear canal with an orientation that is predominantly horizontal, and a rear section positioned behind the external opening of the person's right ear canal with an orientation that is predominantly vertical. The first method also comprises affixing a second set of electrode elements to a left side of the person's head. The second set of electrode elements has an upper section positioned above the external opening of the person's left ear canal with an orientation that is predominantly horizontal, and a rear section positioned behind the external opening of the person's left ear canal with an orientation that is predominantly vertical. The first method also comprises applying an alternating voltage between the first set of electrode elements and the second set of electrode elements. The applying is performed after affixing the first and second sets of electrode elements to the person's head.

In some instances of the first method, the upper section of the first set of electrode elements includes at least three capacitively coupled electrode elements, the rear section of the first set of electrode elements includes at least three capacitively coupled electrode elements, the upper section of the second set of electrode elements includes at least three capacitively coupled electrode elements, and the rear section of the second set of electrode elements includes at least three capacitively coupled electrode elements.

In some instances of the first method, the upper section of each of the first and second sets of electrode elements (a) has a length of at least 6 cm, (b) is positioned less than 6 cm above the external opening of the respective ear canal, (c) has a front end positioned at least 1 cm in front of the external opening of the respective ear canal, and (d) has a rear end positioned at least 1 cm behind the external opening of the respective ear canal.

In some instances of the first method, the rear section of each of the first and second sets of electrode elements (a) has a length of at least 6 cm, (b) is positioned less than 6 cm behind the external opening of the respective ear canal, (c) has an upper end positioned at least 1 cm above the external opening of the respective ear canal, and (d) has a rear end positioned at least 3 cm below the external opening of the respective ear canal.

In some instances of the first method, the upper section of the first set of electrode elements includes at least three capacitively coupled electrode elements, the rear section of the first set of electrode elements includes at least three capacitively coupled electrode elements, the upper section of the second set of electrode elements includes at least three capacitively coupled electrode elements, and the rear section of the second set of electrode elements includes at least three capacitively coupled electrode elements; the upper section of each of the first and second sets of electrode elements (a) has a length of at least 6 cm, (b) is positioned less than 6 cm above the external opening of the respective ear canal, (c) has a front end positioned at least 1 cm in front of the external opening of the respective ear canal, and (d) has a rear end positioned at least 1 cm behind the external opening of the respective ear canal; and the rear section of each of the first and second sets of electrode elements (a) has a length of at least 6 cm, (b) is positioned less than 6 cm behind the external opening of the respective ear canal, (c) has an upper end positioned at least 1 cm above the external opening of the respective ear canal, and (d) has a rear end positioned at least 3 cm below the external opening of the respective ear canal.

Some instances of the first method further comprise affixing a third set of electrode elements having a third centroid to the person's head with the third centroid positioned on top of the person's head; affixing a fourth set of electrode elements having a fourth centroid to the back of the person's neck with the fourth centroid positioned below the person's C2 vertebra and above the person's C7 vertebra; and applying an alternating voltage between the third set of electrode elements and the fourth set of electrode elements, wherein the applying is performed after affixing the third and fourth sets of electrode elements to the person's head. The steps of (a) applying an alternating voltage between the first set of electrode elements and the second set of electrode elements and (b) applying an alternating voltage between the third set of electrode elements and the fourth set of electrode elements are repeated in an alternating sequence. In these instances, the third set of electrode elements may optionally be affixed with the third centroid positioned between 1 and 3 cm anterior to a vertex of the person's head. In these instances, the fourth set of electrode elements may optionally be affixed with the fourth centroid positioned below the person's C3 vertebra and above the person's C6 vertebra. In these instances, the third set of electrode elements may optionally be affixed with the third centroid positioned between 1 and 3 cm anterior to a vertex of the person's head, while the fourth set of electrode elements is affixed with the fourth centroid positioned below the person's C3 vertebra and above the person's C6 vertebra.

In some instances of the first method, the specific locations at which the first and second sets of electrode elements are affixed to the right and left sides of the person's head, respectively, are determined by running finite element simulations for an individual person to calculate a resulting electric field for each combination of positions for the first and second sets of electrode elements; and selecting the combination of positions for the first and second sets of electrode elements that results in the lowest value of $\Psi$, where $\Psi=\sigma T \div MEANT$, $\sigma_T=SD([\mu_i]|i\in\{\alpha, \beta, \gamma, \delta, in\})$, and $MEAN_T=mean([\mu_i]|i\in\{\alpha, \beta, \gamma, \delta, in\})$.

In some instances of the first method, the alternating voltage has a frequency between 100 and 300 kHz.

Another aspect of the invention is directed to a second method of applying an alternating electric field to a brain in a person's body, the body having a mid-coronal plane and a mid-sagittal plane. The second method comprises affixing a first set of electrode elements to the person's head on a right side of the mid-sagittal plane, superior to the external opening of the person's right ear canal; affixing a second set of electrode elements having a second centroid to the person's body on a left side of the mid-sagittal plane and behind the mid-coronal plane, with the second centroid positioned inferior to an external opening of the person's left ear canal, and superior to the person's C7 vertebra; affixing a third set of electrode elements to the person's head on a left side of the mid-sagittal plane, superior to the external opening of the person's left ear canal; and affixing a fourth set of electrode elements having a fourth centroid to the person's body on a right side of the mid-sagittal plane and behind the mid-coronal plane, with the fourth centroid positioned inferior to an external opening of the person's right ear canal, and superior to the person's C7 vertebra. The second method also comprises repeating, in an alternating sequence (a) applying an alternating voltage between the first set of electrode elements and the second set of electrode elements, and (b) applying an alternating voltage between the third set of electrode elements and the fourth set of electrode elements. In the second method, the repeating is performed after affixing the first, second, third, and fourth sets of electrode elements.

In some instances of the second method, the second centroid and the fourth centroid are positioned superior to a midpoint of the person's C2 vertebra. In some instances of the second method, the second centroid and the fourth centroid are positioned inferior to a midpoint of the person's C2 vertebra. In some instances of the second method, the second centroid and the fourth centroid are positioned inferior to the person's C3 vertebra and superior to the person's C6 vertebra.

In some instances of the second method, the specific locations at which the first, second, third, and fourth sets of electrode elements are affixed to the person's body are determined by running finite element simulations for an individual person to calculate a resulting electric field for each combination of positions for the first, second, third, and fourth sets of electrode elements; and selecting the combination of positions for the first, second, third, and fourth sets of electrode elements that results in the lowest value of $\Psi$, where $\Psi=GT \div MEANT$, $\sigma_T=([\mu_i]|i\in\{\alpha, \beta, \gamma, \delta, in\})$, and $MEAN_T=([\mu_i]|i\in\{\alpha, \beta, \gamma, \delta, in\})$.

In some instances of the second method, the alternating voltage has a frequency between 100 and 300 kHz.

Another aspect of the invention is directed to a first apparatus. The first apparatus comprises a flexible backing having an outer side and an inner side, wherein the flexible backing is configured for affixation to a side of a person's head with the inner side facing the person's head. The flexible backing has a first arm with a length of at least 6 cm in a first direction and a second arm with a length of at least 6 cm in a second direction, wherein the second direction is between 65° and 115° away from the first direction. The first apparatus also comprises a first plurality of capacitively coupled electrode elements positioned on the inner side of the first arm of the flexible backing, wherein each of the first plurality of capacitively coupled electrode elements has a conductive plate with a dielectric layer disposed thereon that faces inward; and a second plurality of capacitively coupled electrode elements positioned on the inner side of the second arm of the flexible backing, wherein each of the second plurality of capacitively coupled electrode elements has a conductive plate with a dielectric layer disposed thereon that faces inward. The first apparatus also comprises a first set of conductors that connects to the conductive plates of each of the first plurality of capacitively coupled electrode elements; and a second set of conductors that connects to the conductive plates of each of the second plurality of capacitively coupled electrode elements. The first apparatus also comprises a layer of adhesive positioned to hold portions of the flexible backing that are not covered by any of the electrode elements against the person's head.

In some embodiments of the first apparatus, the first plurality of capacitively coupled electrode elements comprises at least three capacitively coupled electrode elements, and the second plurality of capacitively coupled electrode elements comprises at least three capacitively coupled electrode elements. In some embodiments of the first apparatus, the second direction is between 80° and 100° away from the first direction. In some embodiments of the first apparatus, the second direction is 90° away from the first direction. In some embodiments of the first apparatus, the first plurality of capacitively coupled electrode elements are all wired together in parallel. In some embodiments of the first apparatus, the second plurality of capacitively coupled electrode elements are all wired together in parallel.

Another aspect of the invention is directed to a third method of determining where to position a set of electrode elements on a person's head before the set of electrodes is used to apply an alternating electric field to the person's brain. The third method comprises (a) simulating affixation of a first set of electrode elements to a right side of the person's head at a first plurality of positions, the first set of electrode elements having an upper section positioned above the external opening of the person's right ear canal with an orientation that is predominantly horizontal, and a rear section positioned behind the external opening of the person's right ear canal with an orientation that is predominantly vertical. The third method also comprises (b) simulating affixation of a second set of electrode elements to a left side of the person's head at a second plurality of positions, the second set of electrode elements having an upper section positioned above the external opening of the person's left ear canal with an orientation that is predominantly horizontal, and a rear section positioned behind the external opening of the person's left ear canal with an orientation that is predominantly vertical. The third method also comprises (c) simulating application of an alternating voltage between the first set of electrode elements and the second set of electrode elements at each of the first plurality of positions and at each of the second plurality of positions, respectively. The third method also comprises (d) determining, based on step (c), which of the first plurality of positions and which of the second plurality of positions results in an alternating electric field in the person's brain with high uniformity. The third method also comprises (e) outputting, based on a result of step (d), a recommended position for the first set of electrode elements and a recommended position for the second set of electrode elements.

In some instances of the third method, the upper section of each of the first and second sets of electrode elements (a) has a length of at least 6 cm, (b) is positioned less than 6 cm above the external opening of the respective ear canal, (c) has a front end positioned at least 1 cm in front of the external opening of the respective ear canal, and (d) has a rear end positioned at least 1 cm behind the external opening of the respective ear canal.

In some instances of the third method, the rear section of each of the first and second sets of electrode elements (a) has a length of at least 6 cm, (b) is positioned less than 6 cm behind the external opening of the respective ear canal, (c) has an upper end positioned at least 1 cm above the external opening of the respective ear canal, and (d) has a rear end positioned at least 3 cm below the external opening of the respective ear canal.

Some instances of the third method further comprise (g) simulating affixation of a third set of electrode elements having a third centroid to the person's head at a third plurality of positions with the third centroid positioned on top of the person's head; (h) simulating affixation of a fourth set of electrode elements having a fourth centroid to the back of the person's neck at a fourth plurality of positions with the fourth centroid positioned below the person's C2 vertebra and above the person's C7 vertebra; (i) simulating application of an alternating voltage between the third set of electrode elements and the fourth set of electrode elements at each of the third plurality of positions and at each of the fourth plurality of positions, respectively; (j) determining which of the third plurality of positions and which of the fourth plurality of positions results in an alternating electric field in the person's brain with high uniformity; and (k) outputting, based on a result of step (j), a recommended position for the third set of electrode elements and a recommended position for the fourth set of electrode elements.

In some instances of the third method that include steps (g) through (j), the simulated affixation has the third set of electrode elements affixed with the third centroid positioned between 1 and 3 cm anterior to a vertex of the person's head. In some instances of the third method that include steps (g) through (j), the simulated affixation has the fourth set of electrode elements affixed with the fourth centroid positioned below the person's C3 vertebra and above the person's C6 vertebra.

In some instances of the third method that include steps (g) through (j), the simulated affixation has the third set of electrode elements affixed with the third centroid positioned between 1 and 3 cm anterior to a vertex of the person's head, and the simulated affixation has the fourth set of electrode elements affixed with the fourth centroid positioned below the person's C3 vertebra and above the person's C6 vertebra.

In some instances of the third method, step (d) comprises selecting the combination of positions for the first and second sets of electrode elements that results in the lowest value of $\Psi$, where $\Psi = \sigma_T \div \text{MEAN}_T$, $\sigma_T = \text{SD}([\mu_i] | i \in \{\alpha, \beta, \gamma, \delta, \text{in}\})$, and $\text{MEAN}_T = \text{mean}([\mu_i] | \in \{\alpha, \beta, \gamma, \delta, \text{in}\})$.

Another aspect of the invention is directed to a fourth method of determining where to position a set of electrode elements on a person's body before the set of electrodes is used to apply an alternating electric field to a brain in the person's body. The body has a mid-coronal plane and a mid-sagittal plane. The fourth method comprises (a) simulating affixation of a first set of electrode elements to the person's head at a first plurality of positions on a right side of the mid-sagittal plane, superior to the external opening of the person's right ear canal. The fourth method also comprises (b) simulating affixation of a second set of electrode elements having a second centroid to the person's body at a second plurality of positions on a left side of the mid-sagittal plane and behind the mid-coronal plane, with the second centroid positioned inferior to an external opening of the person's left ear canal, and superior to the person's C7 vertebra. The fourth method also comprises (c) simulating affixation of a third set of electrode elements to the person's head at a third plurality of positions on a left side of the mid-sagittal plane, superior to the external opening of the person's left ear canal. The fourth method also comprises (d) simulating affixation of a fourth set of electrode elements having a fourth centroid to the person's body at a fourth plurality of positions on a right side of the mid-sagittal plane and behind the mid-coronal plane, with the fourth centroid positioned inferior to an external opening of the person's right ear canal, and superior to the person's C7 vertebra. The fourth method also comprises (e) simulating application of an alternating voltage between the first set of electrode elements and the second set of electrode elements at each of the first plurality of positions and at each of the second plurality of positions, respectively. The fourth method also comprises (f) simulating application of an alternating voltage between the third set of electrode elements and the fourth set of electrode elements at each of the third plurality of positions and at each of the fourth plurality of positions, respectively. The fourth method also comprises (g) determining, based on steps (e) and (f), which of the first plurality of positions, which of the second plurality of positions, which of the third plurality of positions, and which of the fourth plurality of positions results in an alternating electric field in the person's brain with high uniformity. And the fourth method also comprises (h) outputting, based on a result of step (g), a recommended position for the first set of electrode elements, a recommended position for the second set of electrode elements, a recommended position for the third set of electrode elements, and a recommended position for the fourth set of electrode elements.

In some instances of the fourth method, the simulated affixation has the second centroid and the fourth centroid positioned superior to a midpoint of the person's C2 vertebra.

In some instances of the fourth method, the simulated affixation has the second centroid and the fourth centroid positioned inferior to a midpoint of the person's C2 vertebra.

In some instances of the fourth method, the simulated affixation has the second centroid and the fourth centroid positioned inferior to the person's C3 vertebra and superior to the person's C6 vertebra.

In some instances of the fourth method, step (g) comprises selecting the combination of positions for the first, second, third, and fourth sets of electrode elements that results in the lowest value of Ψ, where Ψ=σT÷MEANT, σ$_T$=SD([μi] |i∈{α, β, γ, δ, in}), and MEAN$_T$=mean([μ$_i$])|i∈{α, β, γ, δ, in}).

BRIEF DESCRIPTION OF THE DRAWINGS

FIGS. 6A and 6B depict how the brain is divided into five distinct regions α, β, γ, δ, in.

Various embodiments are described in detail below with reference to the accompanying drawings, wherein like reference numerals represent like elements.

DESCRIPTION OF THE PREFERRED EMBODIMENTS

Many types of cancer (e.g., lung, breast, colon, kidney and melanoma) can metastasize to the brain. TTFields can be used to treat and prevent metastases, as described in U.S. Pat. No. 7,599,746.

Because one never knows in advance the exact location within the brain that a metastasis may appear, a good way to prevent or treat metastases is to treat as much of the brain as possible with TTFields. Keeping the field strength as uniform as possible within the entire brain can maximize the percentage of the brain that receives a field strength large enough to prevent or treat the metastases, while preventing the transducer arrays from getting too hot and also conserving battery power. Consistent with these objectives, this application discloses a variety of configurations for arranging the transducer arrays on a person's head to impose TTFields in the brain at field strengths that are as uniform as possible throughout the entire brain (including the infratentorial regions of the brain).

FIGS. 1A-1D depict the conventional layout for positioning transducer arrays on a person's head for treating glioblastoma using TTFields. With this layout, the AC signal generator first applies an AC voltage across the front/back pair of transducer arrays 11, 12, then applies an AC voltage across the right/left pair of transducer arrays 13, 14, and then repeats that two-step sequence for the duration of the treatment. As tabulated below, the uniformity of field intensity for this conventional layout is relatively low. One of the main reasons for the low uniformity is that the field strengths are quite low in the infratentorial regions of the brain.

Figure 1A:
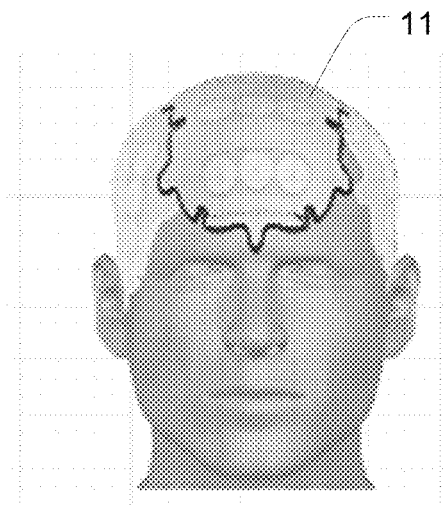
FIGS. 1A-1D depict the conventional layout for positioning transducer arrays on a person's head for treating glioblastoma using TTFields.
Figure 1B:
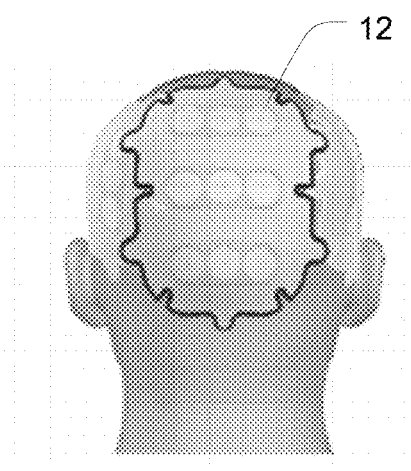
Figure 1C:
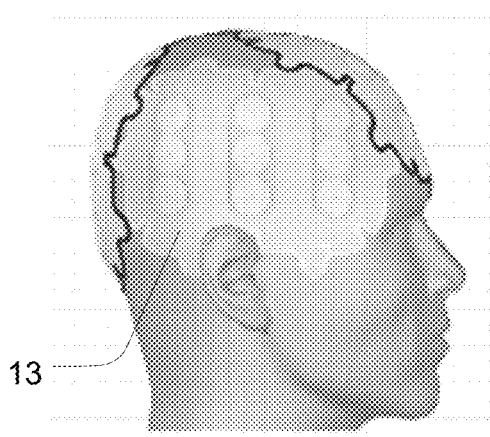
Figure 1D:
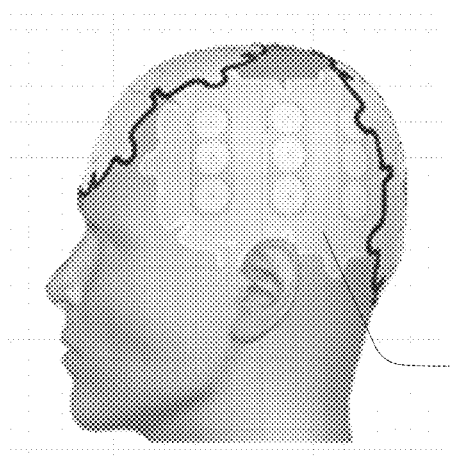
Figure 2A:
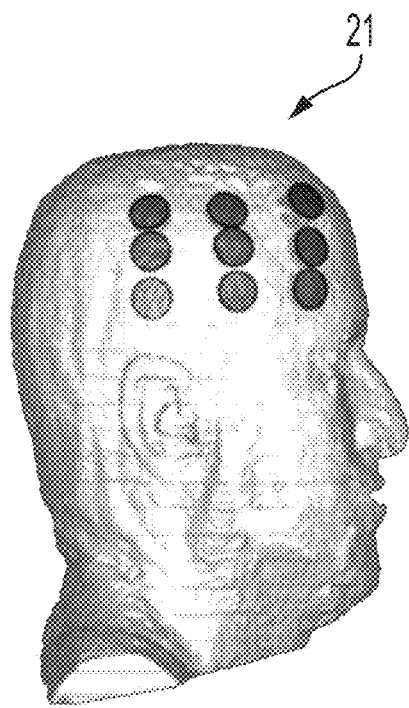
FIGS. 2A-2D depict a set of improved layouts for positioning transducer arrays on a person's head for preventing metastases using TTFields.
Figure 2B:
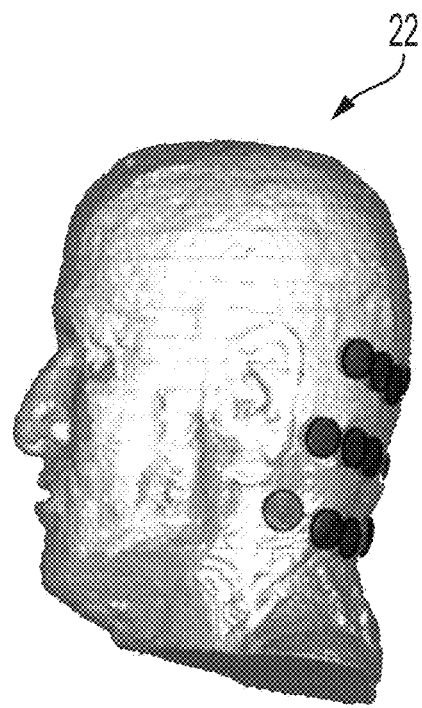
Figure 2C:
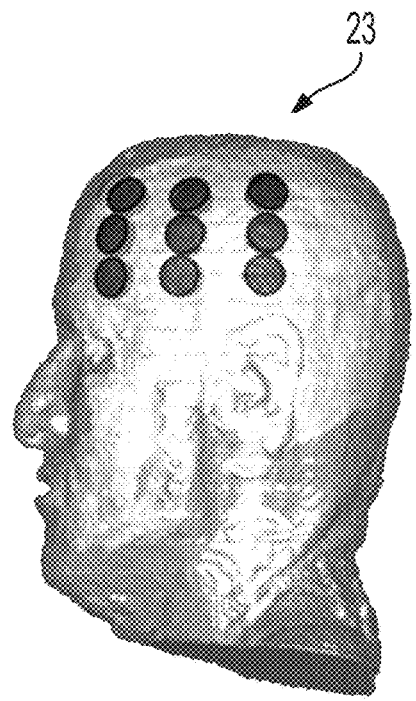
Figure 2D:
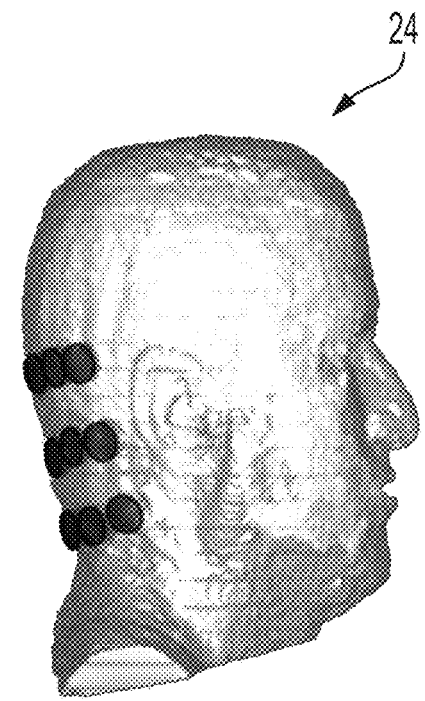

FIGS. 2A-2D depict one set of improved layouts for positioning transducer arrays on a person's head for preventing metastases using TTFields. More specifically, FIG. 2A shows that the first set of electrode elements 21 is affixed to a person's head on a right side of the mid-sagittal plane, superior to the external opening of the person's right ear canal; FIG. 2B shows that the second set of electrode elements 22 is affixed to the person's body on a left side of the mid-sagittal plane and behind the mid-coronal plane, with its centroid positioned inferior to an external opening of the person's left ear canal, and superior to the midpoint of the person's C2 vertebra; FIG. 2C shows that the third set of electrode elements 23 is affixed to the person's head on a left side of the mid-sagittal plane, superior to the external opening of the person's left ear canal; and FIG. 2D shows that the fourth set of electrode elements 24 is affixed to the person's body on a right side of the mid-sagittal plane and behind the mid-coronal plane, with its centroid positioned inferior to an external opening of the person's right ear canal, and superior to the midpoint of the person's C2 vertebra. With this layout, the AC signal generator first applies an AC voltage across the first and second sets of electrode elements 21, 22, then applies an AC voltage across the third and fourth sets of electrode elements 23, 24, and then repeats that two-step sequence for the duration of the treatment. As tabulated below, the uniformity of field intensity for this alternative layout is significantly higher than in the conventional FIG. 1 layout.

Figure 3A:
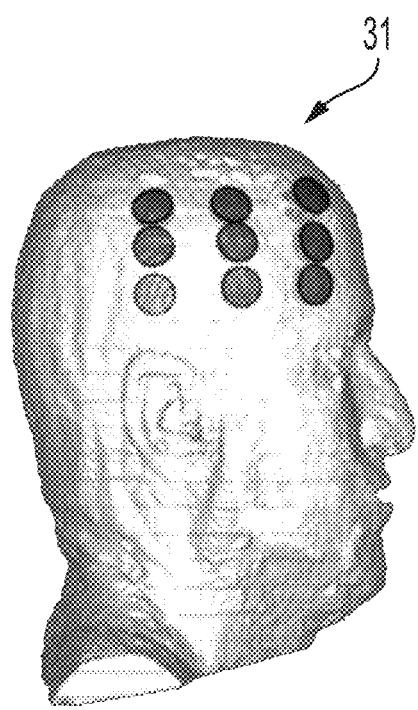
FIGS. 3A-3D depict another set of improved layouts for positioning transducer arrays on a person's head for preventing metastases using TTFields.
Figure 3B:
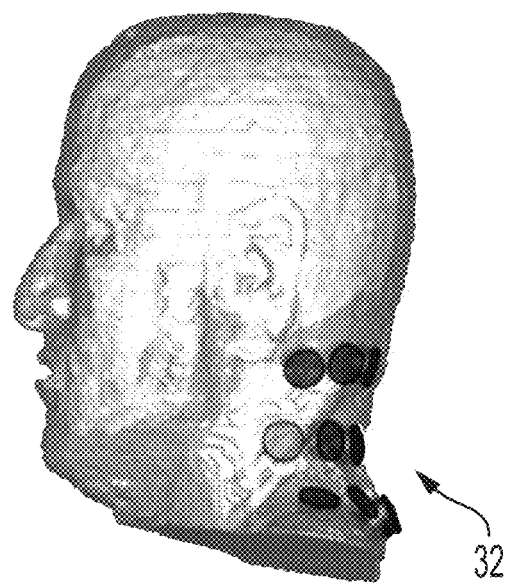
Figure 3C:
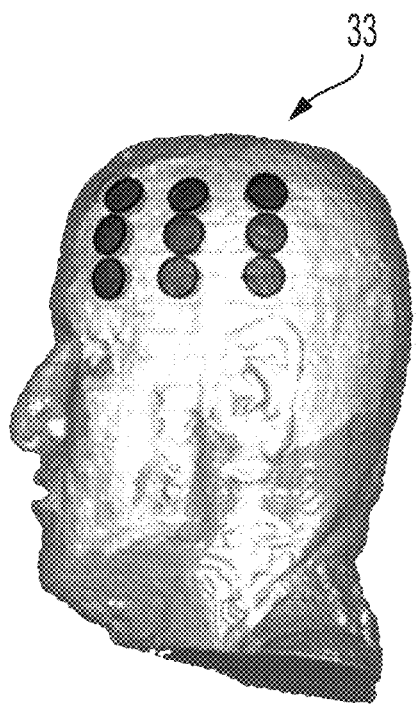
Figure 3D:
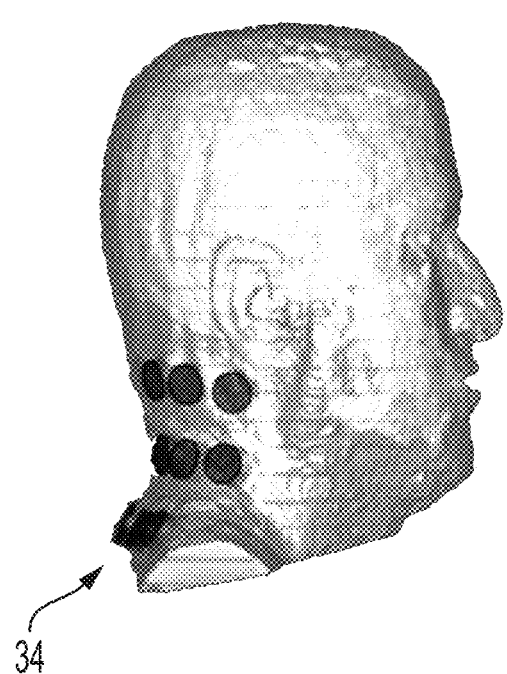

FIGS. 3A-3D depict another set of improved layouts for positioning transducer arrays on a person's head for preventing metastases using TTFields. This layout is similar to the FIG. 2A-2D layout, except that the second and fourth sets of electrode elements 32, 34 are positioned lower down on the person's body. More specifically, FIG. 3A shows that the first set of electrode elements 31 is affixed to a person's head on a right side of the mid-sagittal plane, superior to the external opening of the person's right ear canal; FIG. 3B shows that the second set of electrode elements 32 is affixed to the person's body on a left side of the mid-sagittal plane and behind the mid-coronal plane, with its centroid positioned inferior to the midpoint of the person's C2 vertebra and superior to the person's C7 vertebra; FIG. 3C shows that the third set of electrode elements 33 is affixed to the person's head on a left side of the mid-sagittal plane, superior to the external opening of the person's left ear canal; and FIG. 3D shows that the fourth set of electrode elements 34 is affixed to the person's body on a right side of the mid-sagittal plane and behind the mid-coronal plane, with its centroid positioned interior to the midpoint of the person's C2 vertebra and superior to the person's C7 vertebra. With this layout, the AC signal generator first applies an AC voltage across the first and second sets of electrode elements 31, 32, then applies an AC voltage across the third and fourth sets of electrode elements 33, 34, and then repeats that two-step sequence for the duration of the treatment. As tabulated below, the uniformity of field intensity for this alternative layout is also significantly higher than in the conventional FIG. 1 layout.

Figure 4A:
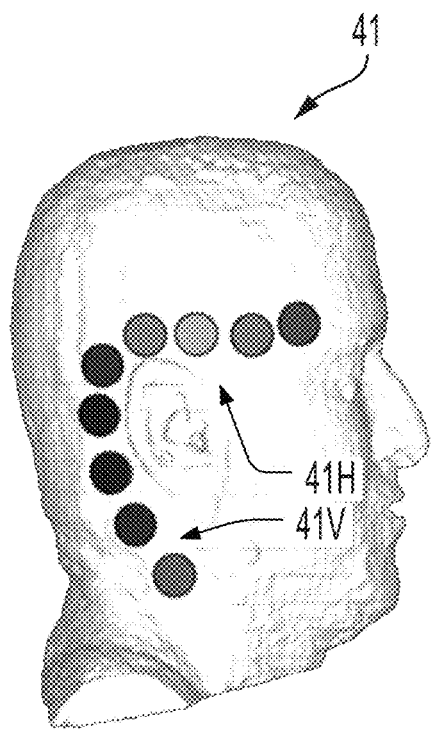
FIGS. 4A-4D depict yet another set of improved layouts for positioning transducer arrays on a person's head for preventing metastases using TTFields.
Figure 4B:
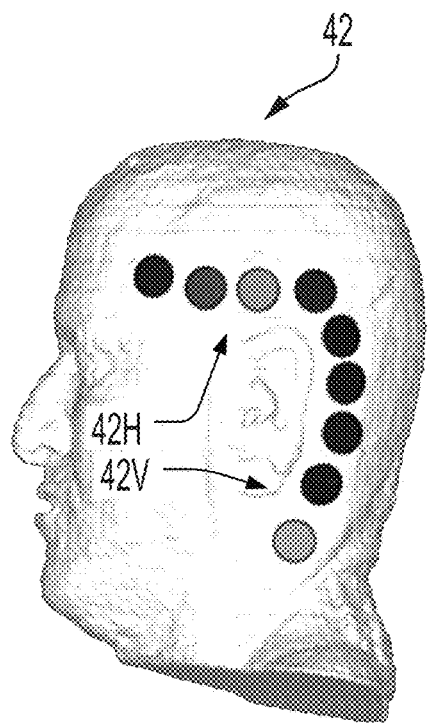
Figure 4C:
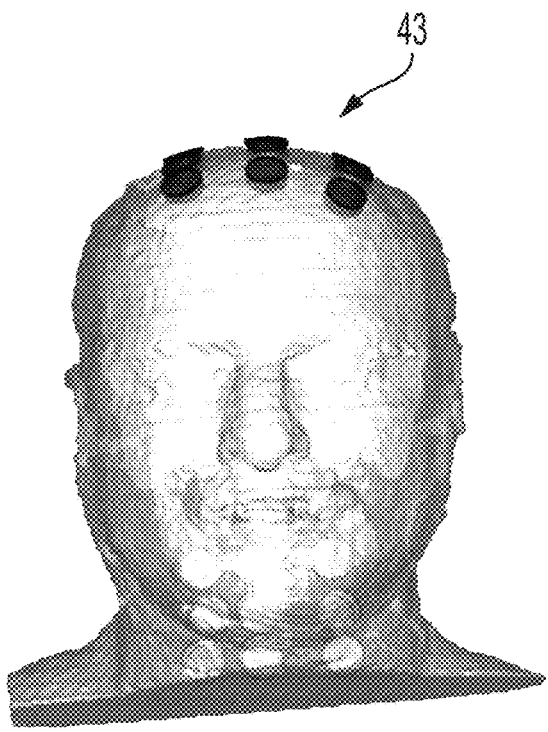
Figure 4D:
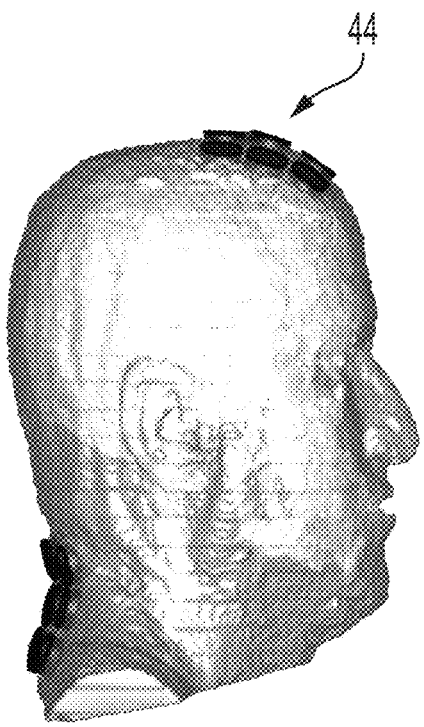

FIGS. 4A-4D depict yet another set of improved layouts for positioning transducer arrays on a person's head for preventing metastases using TTFields. More specifically, FIG. 4A shows that the first set of electrode elements 41 is affixed to a right side of the person's head. The first set of electrode elements 41 has an upper section 41H positioned above (i.e., superior to) the external opening of the person's right ear canal with an orientation that is predominantly horizontal, and a rear section 41V positioned behind the external opening of the person's right ear canal with an orientation that is predominantly vertical. FIG. 4B shows that the second set of electrode elements 42 is affixed to a left side of the person's head. The second set of electrode elements has an upper section 42H positioned above the external opening of the person's left ear canal with an orientation that is predominantly horizontal, and a rear section 42V positioned behind the external opening of the person's left ear canal with an orientation that is predominantly vertical. FIGS. 4C and 4D show that the third set of electrode elements 43 is affixed to the person's head with its centroid positioned on top of the person's head; and FIG. 4D shows that the fourth set of electrode elements 44 is affixed to the back of the person's neck with its centroid positioned below the person's C2 vertebra and above the person's C7 vertebra. With this layout, the AC signal generator first applies an AC voltage across the first and second sets of electrode elements 41, 42, then applies an AC voltage across the third and fourth sets of electrode elements 43, 44, and then repeats that two-step sequence for the duration of the treatment. As tabulated below, the uniformity of field intensity for this alternative layout is also significantly higher than in the conventional FIG. 1 layout.

Optionally, in the FIGS. 4A-4D layout, the upper section 41H of the first set of electrode elements includes at least three capacitively coupled electrode elements, the rear section 41V of the first set of electrode elements includes at least three capacitively coupled electrode elements, the upper section 42H of the second set of electrode elements includes at least three capacitively coupled electrode elements, and the rear section 42V of the second set of electrode elements includes at least three capacitively coupled electrode elements. In alternative embodiments, each of those sections 41H, 41V, 42H, 42V can include a different number of electrode elements (e.g., between 1 and 8).

Optionally, in the FIGS. 4A-4D layout, the upper section of each of the first and second sets of electrode elements (a) has a length of at least 6 cm, (b) is positioned less than 6 cm above the external opening of the respective ear canal, (c) has a front end positioned at least 1 cm in front of the external opening of the respective ear canal, and (d) has a rear end positioned at least 1 cm behind the external opening of the respective ear canal.

Optionally, in the FIGS. 4A-4D layout, the rear section of each of the first and second sets of electrode elements (a) has a length of at least 6 cm, (b) is positioned less than 6 cm behind the external opening of the respective ear canal, (c) has an upper end positioned at least 1 cm above the external opening of the respective ear canal, and (d) has a rear end positioned at least 3 cm below the external opening of the respective ear canal.

Optionally, in the FIGS. 4A-4D layout, the third set of electrode elements is affixed with its centroid positioned between 1 and 3 cm anterior to a vertex of the person's head.

Optionally, in the FIGS. 4A-4D layout, the fourth set of electrode elements is affixed with its centroid positioned below the person's C3 vertebra and above the person's C6 vertebra.

Figure 5:
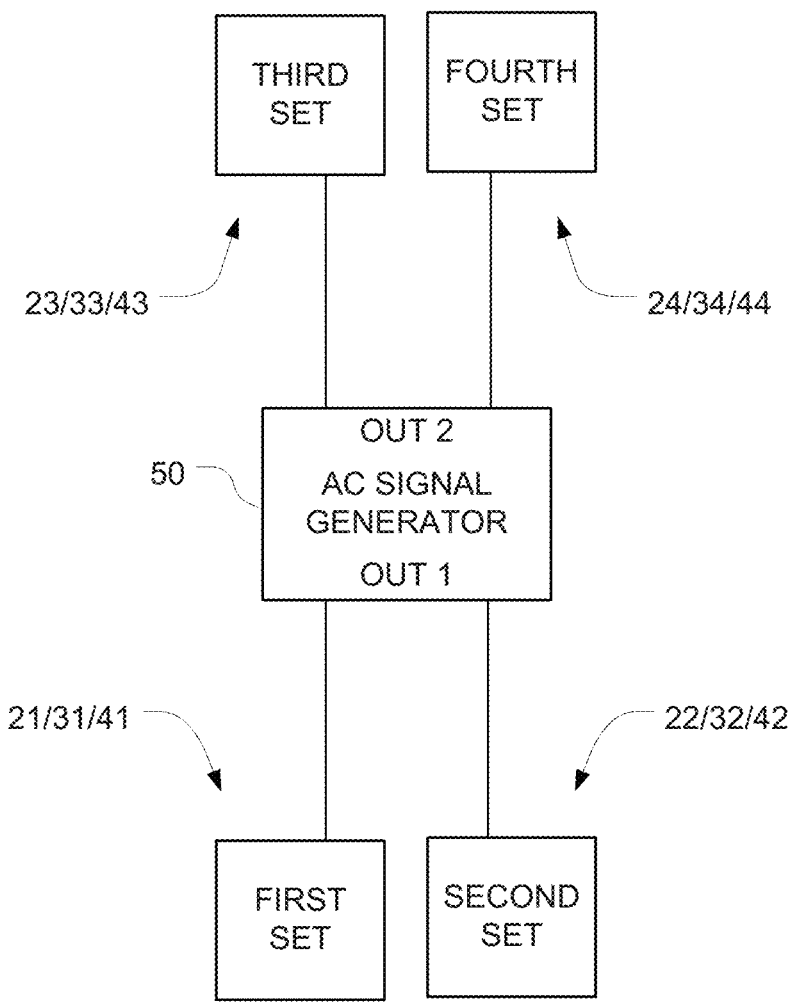
FIG. 5 depicts a block diagram of a system that may be used to apply the AC voltage across the sets of electrode elements depicted in FIGS. 2, 3, and 4.

FIG. 5 depicts a block diagram of a system that includes an AC voltage generator 50 that may be used to apply the AC voltage across the first and second sets of electrode elements (21/22, 31/32, and 41/42 in FIGS. 2, 3, and 4, respectively) and across the third and fourth sets of electrode elements (23/24, 33/34, and 43/44 in FIGS. 2, 3, and 4, respectively) in an alternating sequence as described above in connection with FIGS. 2-4 above.

Figure 6A:
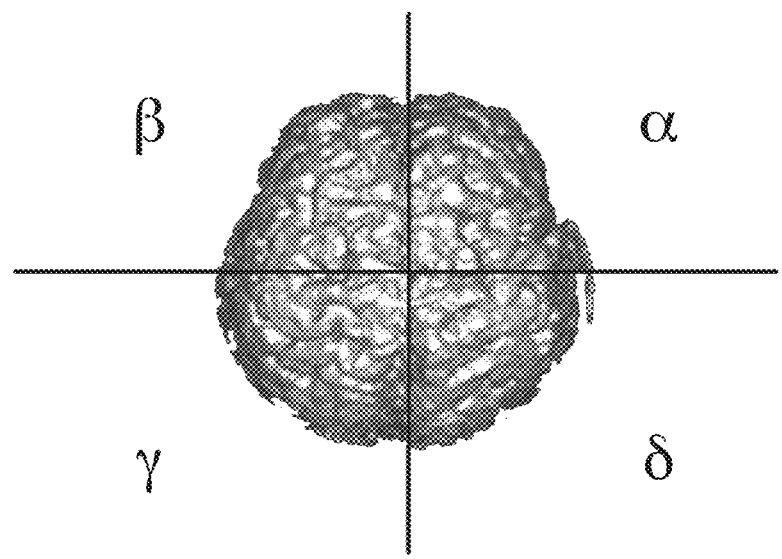
Figure 6B:
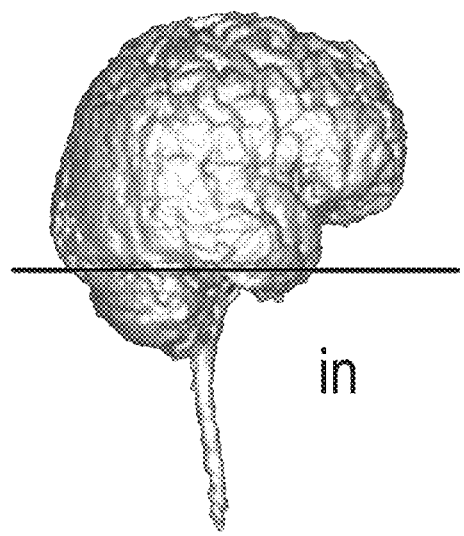

For each of the transducer array layouts depicted above, electric fields were simulated using a realistic human head model extending as far as the shoulders. In the simulations, transducer arrays with 9 capacitively coupled disc-shaped electrode elements, each having a diameter of 2 cm, were placed on the locations on the body described above in connection with FIGS. 1-4, and a constant current of 2 A peak-to-peak with a 200 kHz frequency was applied to the outer surfaces of the disks. The simulations were performed using Sim4Life version 4 platform (ZMT-Zurich). To analyze the uniformity of the electric field, the brain was divided into five compartments as depicted in FIGS. 6A-6B: the infratentorial areas "in" (including the cerebellum and brain stem), and four compartments for the upper brain—front-right α, front-left β, rear-left γ, and rear-right δ. The boundaries between these regions of the brain are depicted in FIGS. 6A-6B. The field intensity was calculated for each voxel in each of the five compartments using finite element simulation. For each compartment the mean and median field intensities of all voxels in the compartment were calculated. Data was taken only for grey and white matter cells.

For each pair of transducer arrays in each of the layouts depicted above, Ψ was defined as the standard deviation between the mean of the different compartments divided by the average of the different compartments, as follows.

$$\Psi = \frac{\sigma_T}{MEAN_T}$$

where $\sigma_T = SD([\mu_i] | i \in \{\alpha, \beta, \gamma, \delta, in\})$;
and $MEAN_T = mean([\mu_i] | i \in \{\alpha, \beta, \gamma, \delta, in\})$ In these three equations, SD stands for standard deviation; μi is the mean of each compartment; α, β, γ, δ are the cerebral compartments (see FIG. 6A); and "in" is the cerebellum/brain stem compartment (see FIG. 6B).

The value of Ψ obtained (in percent) for each individual pair of transducer arrays are presented in Table 1 below.

TABLE 1

|  | FIGS. | | | | | | | |
| --- | --- | --- | --- | --- | --- | --- | --- | --- |
|  | 1A/1B | 1C/1D | 2A/2B | 2C/2D | 3A/3B | 3C/3D | 4A/4B | 4C/4D |
| Electrodes | 11/12 | 13/14 | 21/22 | 23/24 | 31/32 | 33/34 | 41/42 | 43/44 |
| Ψ [%] | 29.38* | 29.38 | 17.19 | 20.16 | 27.25 | 28.8 | 15.55 | 15.48 |

*The value for the FIGS. 1A-1B layout was estimated.

Based on the results in Table 1, when only a single pair of transducer arrays is used to impose a field in a person's brain, the two best layouts for positioning the transducer arrays to obtain the highest uniformity throughout the brain are the layouts 43/44 (depicted in FIGS. 4C/4D); and the layouts 41/42 (depicted in FIGS. 4A/4B).

Next, for each set of the transducer array layouts depicted in FIGS. 1-4, the uniformity of the field created throughout the brain was evaluated by using finite element simulation to calculate the field strength at each voxel in the brain in the following two situations: (a) when an AC voltage is applied across the first and second sets of electrode elements (11/12, 21/22, 31/32, and 41/42, in FIGS. 1, 2, 3, and 4, respectively), and (b) when an AC voltage is applied across the third and fourth sets of electrode elements (13/14, 23/24, 33/34, and 43/44, in FIGS. 1, 2, 3, and 4, respectively). Then, for each voxel in the brain, the field strength result for situation (a) and the field strength result for situation (b) were averaged.

After obtaining the average field strength at each voxel in the brain, Ψ was calculated using the same three equations that were used to calculate Ψ described above in connection with Table 1. Except this time, instead of using a single field strength for each voxel in the brain as the input to the equations, an average of two field strengths for each voxel in the brain was used as the input to the equations.

The value of Ψ obtained for each set of four transducer arrays (in percent) are presented in Table 2 below. These values are based on the assumption that the field is applied between the first and second transducer arrays in any given set half the time, and between the third and fourth transducer arrays in the given set the other half of the time.

TABLE 2

| | FIGS. | | | |
|---|---|---|---|---|
| | 1A-1D | 2A-2D | 3A-3D | 4A-4D |
| Electrode pairs that were averaged | 11/12 and 13/14 | 21/22 and 23/24 | 31/32 and 33/34 | 41/42 and 43/44 |
| Ψ [%] | 29.38* | 5.23 | 8.21 | 3.03 |

*The result for the FIGS. 1A-1D layout relies on the estimate identified above in connection with Table 1.

Based on the results in Table 2, when two pairs of transducer arrays are used to impose a field in a person's brain, with each pair being energized 50% of the time in an alternating sequence, the two best layouts for positioning the transducer arrays to obtain the highest uniformity throughout the brain are (1) the layouts 41/42 combined with 43/44 (as depicted in FIGS. 4A-4D); and (2) the layouts 21/22 combined with 23/24 (as depicted in FIGS. 2A-2D).

Additional data for the transducer array layouts depicted above in FIGS. 2-4 are provided below. For the positioning of the transducer arrays 21/22 depicted in FIGS. 2A/2B, the data was as shown below in Table 3.

TABLE 3

| | α | β | γ | δ | in |
|---|---|---|---|---|---|
| Mean intensity (V/cm) | 2.02 | 1.83 | 1.23 | 1.76 | 1.69 |
| Median intensity (V/cm) | 2.03 | 1.81 | 1.22 | 1.64 | 1.66 |
| % volume over 1 V/cm | 98.11 | 98.70 | 80.76 | 95.47 | 95.78 |
| Standard Deviation | 0.52 | 0.42 | 0.25 | 0.60 | 0.40 |

For the positioning of the transducer arrays 23/24 depicted in FIGS. 2C/2D the data was as shown below in Table 4.

TABLE 4

| | α | β | γ | δ | in |
|---|---|---|---|---|---|
| Mean intensity (V/cm) | 1.15 | 1.64 | 2.05 | 1.87 | 1.69 |
| Median intensity (V/cm) | 1.14 | 1.49 | 2.06 | 1.86 | 1.68 |
| % volume over 1 V/cm | 71.15 | 90.76 | 98.34 | 98.92 | 93.51 |
| Standard Deviation | 0.24 | 0.59 | 0.53 | 0.41 | 0.44 |

For the positioning of the transducer arrays 31/32 depicted in FIGS. 3A/3B, the data was as shown below in Table 5.

TABLE 5

| | α | β | γ | δ | in |
|---|---|---|---|---|---|
| Mean intensity (V/cm) | 2.20 | 1.73 | 1.20 | 1.15 | 1.62 |
| Median intensity (V/cm) | 2.22 | 1.69 | 1.17 | 1.11 | 1.61 |
| % volume over 1 V/cm | 98.46 | 97.12 | 74.30 | 68.44 | 97.55 |
| Standard Deviation | 0.60 | 0.44 | 0.29 | 0.28 | 0.30 |

For the positioning of the transducer arrays 33/34 depicted in FIGS. 3C/3D the data was as shown below in Table 6.

TABLE 6

| | α | β | γ | δ | in |
|---|---|---|---|---|---|
| Mean intensity (V/cm) | 1.12 | 1.07 | 2.13 | 1.71 | 1.58 |
| Median intensity (V/cm) | 1.08 | 1.03 | 2.13 | 1.68 | 1.58 |
| % volume over 1 V/cm | 64.55 | 56.06 | 98.48 | 95.83 | 96.07 |
| Standard Deviation | 0.29 | 0.28 | 0.57 | 0.46 | 0.32 |

For the positioning of the transducer arrays 41/42 depicted in FIGS. 4A/4B, the data was as shown below in Table 7.

TABLE 7

| | α | β | γ | δ | in |
|---|---|---|---|---|---|
| Mean intensity (V/cm) | 1.16 | 1.57 | 1.28 | 1.65 | 1.65 |
| Median intensity (V/cm) | 1.16 | 1.52 | 1.31 | 1.64 | 1.72 |
| % volume over 1 V/cm | 70.26 | 86.89 | 76.03 | 91.69 | 94.10 |
| Standard Deviation | 0.32 | 0.50 | 0.37 | 0.47 | 0.39 |

For the positioning of the transducer arrays 43/44 depicted in FIGS. 4C/4D the data was as shown below in Table 8.

TABLE 8

| | α | β | γ | δ | in |
|---|---|---|---|---|---|
| Mean intensity (V/cm) | 1.94 | 1.48 | 2.01 | 1.47 | 1.56 |
| Median intensity (V/cm) | 1.89 | 1.44 | 1.99 | 1.43 | 1.53 |
| % volume over 1 V/cm | 98.70 | 94.82 | 98.58 | 94.47 | 97.00 |
| Standard Deviation | 0.54 | 0.34 | 0.57 | 0.35 | 0.32 |

In the embodiments depicted in FIGS. 2, 3, and 4C/4D, each set of electrode elements is configured as a 3×3 array of individual electrode element discs. As a result, in these embodiments, the centroid of the respective set will coincide with the center of the center disc. But in alternative embodiments, each set of electrode elements may include a different number of electrode elements. For example, a given set of electrode elements may be configured as a 2×2 array of individual electrode element discs. In this situation, the centroid could be in a region that is located between all four disks. In other alternative embodiments, a given set of electrode elements may include only a single electrode element disc (which may be any suitable shape including but not limited to round and rectangular). In this situation, the centroid would coincide with the center of that single electrode element.

In the embodiments depicted in FIGS. 2-5, all four sets of electrode elements are preferably capacitively coupled to the person's body. After affixing the first, second, third, and fourth sets of electrode elements as described above for the respective embodiments, the following steps are repeated in an alternating sequence: (a) applying an alternating voltage between the first set of electrode elements and the second set of electrode elements, and (b) applying an alternating voltage between the third set of electrode elements and the fourth set of electrode elements. In some embodiments, the frequency of these alternating voltages is between 100 kHz and 300 kHz.

For the embodiments described above in connection with FIGS. 2-5, the values provided in Tables 1-7 were obtained by simulating the electric fields that are obtained when each of the four sets of electrode elements was positioned as depicted in FIGS. 2-4. Note, however, that the positions of each set of electrode elements may be varied from the exact locations depicted in those figures, as long as the movement is small enough so that the respective anatomic description above remains unchanged. For example, the first set of electrode elements 21 depicted in FIG. 2A can move up, down, or to either side, as long as it remains affixed to a person's head on a right side of the mid-sagittal plane, superior to the external opening of the person's right ear canal. Similarly, the second set of electrode elements 22 depicted in FIG. 2B can move up, down, or to either side, as long as it remains affixed to the person's body on a left side of the mid-sagittal plane and behind the mid-coronal plane, with its centroid positioned inferior to an external opening of the person's left ear canal, and superior to the midpoint of the person's C2 vertebra. Within this limited range of movement, the optimum position of each of the four sets of electrode elements may be determined using simulations (e.g., finite element simulations) for each individual person to calculate the resulting electric field for each combination of positions for the various sets of electrodes, and selecting the combination that provides the best results (e.g., the highest uniformity of the field throughout the brain, or the smallest Ψ). An indication of the selected combination is then output to the care provider using, for example, a suitable display or printout. The care provider will then apply the sets of electrode elements to the person at the positions indicated by the output, hook the sets of electrode elements up to the AC signal generator 50, and commence treatment.

Figure 7:
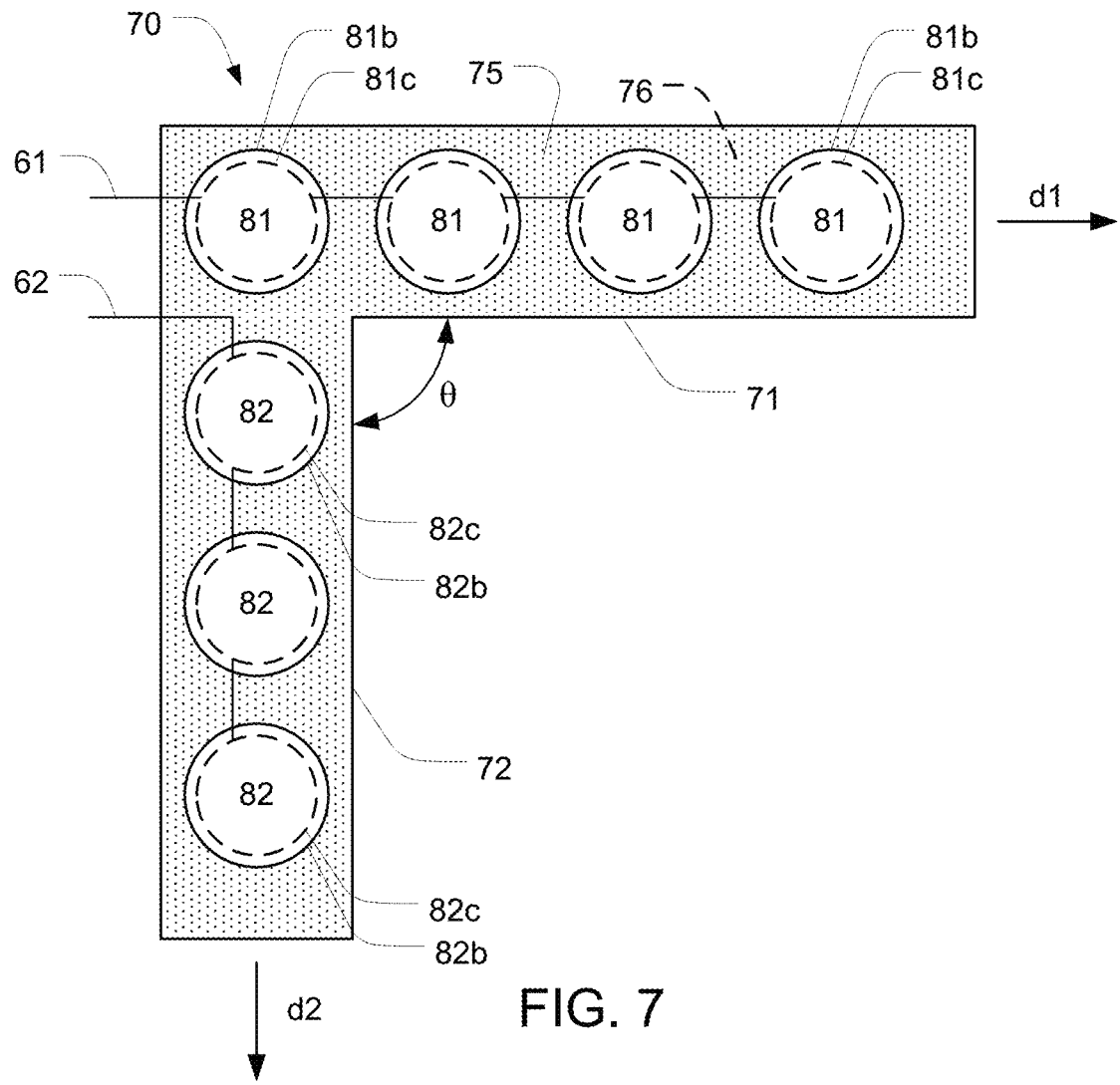
FIG. 7 depicts an apparatus that may be used for each of the sets of electrode elements shown in FIGS. 4A and 4B.

FIG. 7 depicts an apparatus that may be used to implement either the first set of electrode elements 41 that is affixed to the right side of the person's head (shown in FIG. 4A) or the second set of electrode elements 42 that is affixed to the left side of the person's head (shown in FIG. 4B).

This apparatus is used for applying an alternating electric field to a person's brain, and it comprises a flexible backing 70 having an outer side 76 (hidden in FIG. 7) and an inner side 75. The flexible backing 70 is configured for affixation to a side of the person's head with the inner side 75 facing the person's head. Suitable materials for the flexible backing include cloth, foam, and flexible plastic (e.g., similar to corresponding materials used in bandages). The flexible backing has a first arm 71 with a length of at least 6 cm in a first direction d1 and a second arm with a length of at least 6 cm in a second direction d2.

A first plurality of capacitively coupled electrode elements 81 is positioned on the inner side 75 of the first arm 71 of the flexible backing 70, and each of the first plurality of capacitively coupled electrode elements 81 has a conductive plate 81c with a dielectric layer 81b disposed thereon that faces inward. A second plurality of capacitively coupled electrode elements 82 is positioned on the inner side 75 of the second arm 72 of the flexible backing 70, and each of the second plurality of capacitively coupled electrode elements 82 has a conductive plate 82c with a dielectric layer 82b disposed thereon that faces inward. The electrode elements 81, 82 may be similar to the conventional electrode elements used in the Novocure Optune® system. Optionally, temperature sensors (e.g., thermistors) may be positioned beneath some or all of the electrode elements 81, 82 in a manner that is similar to the conventional arrangement used in the Novocure Optune® system.

A first set of conductors 61 connects to the conductive plates 81c of each of the first plurality of capacitively coupled electrode elements 81 in parallel, and a second set of conductors 62 connects to the conductive plates 82c of each of the second plurality of capacitively coupled electrode elements 82 in parallel. The conductors 62 may be implemented using, for example, discrete wiring or using traces on a flex circuit. A layer of adhesive (indicated by the dotted pattern) is positioned on the inner side 75 of the flexible backing 70, and this adhesive is configured to hold portions of the flexible backing 70 that are not covered by any of the electrode elements 81, 82 against the person's head.

In the embodiment depicted in FIG. 7, the first plurality of electrode elements 81 has four electrode elements and the second plurality of electrode elements 82 has three electrode elements. However, in alternative embodiments, the number of electrode elements in each of the first and second pluralities of electrode elements can vary (e.g., between 2 and 10).

In the embodiment depicted in FIG. 7, the angle θ between the first direction d1 and the second direction d2 is 90°. However, in alternative embodiments, that angle θ can be between 80° and 100°, or between 65° and 115°.

Note that in the orientation depicted in FIG. 7, the apparatus is suited for use as the second set of electrodes 42 that is positioned next to the left ear in FIG. 4B, with the first and second pluralities of electrode elements 81, 82 in FIG. 7 corresponding to the upper/horizontal arm 42H and the rear/vertical arm 42V, respectively, in FIG. 4B. But if the backing 70 is rotated clockwise by 90° with respect to the orientation shown in FIG. 7, the same apparatus would then be suited for use as the first set of electrodes 41 that is positioned next to the right ear in FIG. 4A. More specifically, after a 90° clockwise rotation, the first plurality of electrode elements 81 in FIG. 7 would correspond to the rear/vertical arm 41V in FIG. 4A, and the second plurality of electrode elements 82 in FIG. 7 would correspond to the upper/horizontal arm 41H in FIG. 4A.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:
1. An apparatus comprising:
a flexible backing having an outer side and an inner side, wherein the flexible backing is configured for affixation to a side of a person's head with the inner side facing the person's head, the flexible backing having a first arm and a second arm, wherein the first and second arms each extend at least 6 cm from a common point in respective first and second directions, and wherein the second direction is between 65° and 115° away from the first direction;

a first plurality of capacitively coupled electrode elements positioned on the inner side of the first arm of the flexible backing, wherein each of the first plurality of capacitively coupled electrode elements has a conductive plate with a dielectric layer disposed thereon that faces inward;

a second plurality of capacitively coupled electrode elements positioned on the inner side of the second arm of the flexible backing, wherein each of the second plurality of capacitively coupled electrode elements has a conductive plate with a dielectric layer disposed thereon that faces inward;

a first set of conductors that connects to the conductive plates of each of the first plurality of capacitively coupled electrode elements;

a second set of conductors that connects to the conductive plates of each of the second plurality of capacitively coupled electrode elements; and a layer of adhesive positioned to hold portions of the flexible backing that are not covered by any of the electrode elements against the person's head.

2. The apparatus of claim 1, wherein the first plurality of capacitively coupled electrode elements comprises at least three capacitively coupled electrode elements, and the second plurality of capacitively coupled electrode elements comprises at least three capacitively coupled electrode elements.

3. The apparatus of claim 1, wherein the second direction is between 80° and 100° away from the first direction.

4. The apparatus of claim 1, wherein the second direction is 90° away from the first direction.

5. The apparatus of claim 1, wherein the first plurality of capacitively coupled electrode elements are all wired together.

6. The apparatus of claim 1, wherein the second plurality of capacitively coupled electrode elements are all wired together.

7. The apparatus of claim 1, wherein the flexible backing has no electrode elements positioned thereon other than the first plurality of electrode elements positioned on the first arm and the second plurality of electrode elements positioned on the second arm.

8. The apparatus of claim 7, wherein the first plurality of electrode elements positioned on the first arm are all positioned in a first substantially straight single line and the second plurality of electrode elements positioned on the second arm are all positioned in a second substantially straight single line.

9. The apparatus of claim 1, wherein the first plurality of electrode elements positioned on the first arm and the second plurality of electrode elements positioned on the second arm include all electrode elements positioned on the flexible backing.

10. The apparatus of claim 9, wherein the first plurality of electrode elements positioned on the first arm are all positioned in a first substantially straight single line and the second plurality of electrode elements positioned on the second arm are all positioned in a second substantially straight single line.

11. The apparatus of claim 1, wherein the first plurality of electrode elements positioned on the first arm are all positioned in a first substantially straight single line and the second plurality of electrode elements positioned on the second arm are all positioned in a second substantially straight single line.

* * * * *